(12) United States Patent
Safko et al.

(10) Patent No.: US 9,414,955 B2
(45) Date of Patent: Aug. 16, 2016

(54) BACK SUPPORT DEVICE

(71) Applicant: American Ingenuity LLC, New York, NY (US)

(72) Inventors: Ronald Safko, New York, NY (US); Jack Schwartz, New York, NY (US)

(73) Assignee: American Ingenuity, LLC

( * ) Notice: Subject to any disclaimer, the term of this patent is extended or adjusted under 35 U.S.C. 154(b) by 0 days.

(21) Appl. No.: 14/813,198

(22) Filed: Jul. 30, 2015

(65) Prior Publication Data

US 2016/0045355 A1 Feb. 18, 2016

Related U.S. Application Data (60) Provisional application No. 62/037,287, filed on Aug. 14, 2014.

(51) Int. Cl.
*A61F 5/02* (2006.01)

(52) U.S. Cl.
CPC ..................... *A61F 5/028* (2013.01)

(58) Field of Classification Search
CPC .......... A61F 5/024; A61F 13/14; A61F 5/03; A61F 5/026; A61F 5/028; A61F 5/3769; A61F 5/3792; A47D 15/008
See application file for complete search history.

(56) References Cited

U.S. PATENT DOCUMENTS

| | | | | |
|---|---|---|---|---|
| 3,441,027 A | * | 4/1969 | Lehman | A41C 1/08 450/123 |
| 5,179,942 A | * | 1/1993 | Drulias | A61F 5/028 128/101.1 |
| 5,257,419 A | * | 11/1993 | Alexander | A61F 5/028 2/338 |
| 5,484,395 A | | 1/1996 | DeRoche | |
| 6,068,606 A | | 5/2000 | Castel et al. | |
| 6,766,532 B1 | | 7/2004 | Cabana | |
| 6,962,572 B1 | | 11/2005 | Zahiri | |
| 7,134,969 B2 | | 11/2006 | Citron et al. | |
| 7,651,163 B2 | | 1/2010 | Jaskot et al. | |
| 8,226,587 B2 | | 7/2012 | Segal et al. | |
| 8,449,484 B2 | | 5/2013 | Johnson | |
| 8,708,834 B1 | | 4/2014 | Domangue | |

* cited by examiner

*Primary Examiner* — Ophelia A Hawthorne
(74) *Attorney, Agent, or Firm* — Mitchell J. Mehlman, Esq.

(57) ABSTRACT

Devices and methods for improved lumbar-pelvic-hip support for active individuals are provided. Devices can include a body having tapered ends for fastening said body about a user's torso. X shaped members can be configured to bisect the body. A longitudinal reinforcement member can be configured to bisect one or more X shaped members and a pair of elastic straps can be connected to the body for providing lumbar-pelvic-hip support to a user.

8 Claims, 6 Drawing Sheets

BACK SUPPORT DEVICE

CROSS-REFERENCE TO RELATED APPLICATION

This application claims priority of U.S. Provisional Patent Application Ser. No. 62/037,287, entitled "Back Support Device", and filed Aug. 14, 2014, the disclosure of which is incorporated herein by reference in its entirety.

BACKGROUND OF THE INVENTION

Various attempts have been made to overcome the problem of protecting and supporting the lower back during strenuous or athletic activities that require support and flexibility. In addition to being employed for the game of golf, support devices are often used in many other sports such as tennis, baseball, football, and the like.

The inventions as disclosed and described herein are designed to enhance a sports player's ability, offering secure comfort for those who may or may not have low back or hip orthopedic conditions.

The object of the golf swing is to hit the ball as long and as accurately as possible. The swing requires rotation with extension of the lumbar spine coupled with pelvic torque. These swing elements could lead to creating or exacerbating spine or hip orthopedic conditions, especially if they are accompanied by poor posture and a structural imbalance. Swinging the golf club with a painful back is not conducive to accurately hitting the ball for distance or for enjoying the sport.

The present invention considers these imbalances and provides improved core and trunk alignment, which can translate into a less painful, more relaxed, smoother, balanced, and controlled swing.

Contrary to popular belief, chronic back, neck or shoulder pain does not always originate in the back. In fact, a large majority of back, neck, hip, and leg pain, along with most muscle strain, can be traced to two natural biomechanical phenomena; gravity and balance.

The center of gravity within the human body focuses on the sacroiliac joints in the pelvis, the body's two primary weight-bearing joints. Core muscles link the upper and lower body, thus, a strong core, particularly the pelvis, is essential to enhanced performance and stability.

The lumbar-pelvic-hip complex consists of the fourth and fifth lumbar joints, the sacrum, the two hip joints, and the pubic symphysis. This complex should always be considered as a mechanical unit, and the position of the pelvis is the keynote in postural alignment. Involvement in one structure affects the positioning and movement of the others.

Any frontal plane asymmetry, leg-length discrepancy, or loss of motion in one joint of the complex that might alter the forces from the spine above or the lower limbs below, can influence the lumbar-pelvic-hip complex, an result in abnormal mechanical stresses and symptoms of overuse causing pain and limited movement.

The "core" consists of the spine, trunk (upper, lower, front, back and sides) and pelvis connection. The pelvis is perhaps the most important component of both the core and the lumbar-pelvic-hip complex. There are many deep internal muscles in our trunk and pelvis as well as surrounding our spine.

These muscles act as stabilizers. A stable core is largely dependent on our individual posture which is affected by our movement habits and patterns. The level of core strength a person has depends on a person's posture and muscle balance.

The human body is built to receive forces we place on it in relation to gravity; the job of the core helps to support, power, and distribute these forces in the desired direction by activating the particular muscle groups for the required action. The type of posture each individual exhibits will determine how these forces are distributed. If there is uneven distribution of load, this typically results in the body overcompensating i.e. over and/or under-utilizing of muscles.

Very few humans maintain perfect posture throughout their entire lives. Sitting, standing, carrying, lifting, the structural shape of the spine, and injuries, are a few of the factors that affect posture, muscle balance and the body's spatial awareness.

Research has shown that when the pelvis area is out of balance, it will cause abnormal stress to one side of the body, forcing muscles to strain, and affecting strength, endurance and overall performance. As one ages, wear and tear on the pelvic bones and joints (including the sacroiliac joints, integral components of the lumbar-pelvic-hip complex, which change as we age) may cause significant problems, may present as back pain, and will demand increased support in this region.

A common ailment involving the lumbar-pelvic-hip complex is sacroiliac dysfunction. The clinical signs are pain and local tenderness, with increased pain on position changes such as ascending or descending stairs or slopes or rising from sitting or lying to standing. Pain may also increase with prolonged postures in sitting or standing positions. It has been shown that dysfunctions of the pelvis often are associated with hip, buttocks, and groin pain syndromes. Since joint stability is critical for optimal function, impaired or altered sacral movement (e.g. nutation and counter-nutation) and coupled with inadequate "form and force closure" of the sacroiliac joints is seen as an important cause of pelvic dysfunction.

By protecting the sacroiliac joints and ligaments with an appropriate support, pain can be minimized and normal function can be achieved. Control of sacral movement increases stability and reduces the pain caused by friction in the sacroiliac joint(s).

Force closure is defined as stability created by the muscular system. Form closure is defined as the stability created by the joint surfaces, shape of the bone and ligamentous integrity. Nutation is sacral flexion which occurs with trunk flexion or hip extension. Counter-nutation is sacral extension which occurs with trunk extension or hip flexion.

The combination of for and force closure creates a self-locking mechanism that stabilizes the SI joint during loading. Muscular imbalance weakness and inadequate coordination between muscles diminish force closure and disrupts sacral motion which consequently increases the load on the pelvic ligaments, straining those ligaments, which results in pain and laxity.

The present invention supports the hips and pelvis, helping with alignment and balance, allowing for better flexibility and stability during activity and enhanced force closure, which leads to enhanced form closure.

The instant invention allows active people to move and function successfully, despite their specific pain or discomfort, and may help prevent further injury.

Advantages include; simultaneous stabilization and support of back and hips; improved core and trunk alignment; relief for back, hip and leg pain; prevention of muscle spasms and cramping; faster recovery of overused muscles; structural support for weak or injured backs and hips; prevention of harmful movements; enhanced strength and muscle tone of injured muscles; correction of joint problems; adjustment of misalignments that result from tightened muscles; facilitation of joint motion; comfort, control and confidence for every physical activity; and improved postural awareness.

Back pain is one of the most common reasons people visit their doctor. Eight out of ten people have some type of backache today. Americans spend $86 billion a year on spine treatments (up 65% in a decade); about the same as we spend treating cancer, yet our backs are not getting better. The percentage of back pain sufferers has increased and more of them are reporting physical, social and work limitations.

Some known devices include U.S. Pat. No. 6,068,606 which discloses a back support brace comprising a back panel, a left side panel and a right side panel wherein the left and right side panels are secured at opposite ends of the back panel and are wrappable around the waist of a wearer and adjustably securable thereto. Aligned pairs of belt loops are provided on an inner surface of the brace and are adapted to receive a belt for holding up the pants of the wearer of the brace therethrough so as to prevent the brace from being advanced out of a preset position during lifting activities.

U.S. Pat. No. 5,484,395 is directed to a back brace including a lumbar spinal support belt disposed about a user's torso by a first co-acting fastening means, a strap-like tensioning member pair affixed to the lumbar spinal support belt and being wrapped about the user's torso using a second co-acting fastening means, manual engagement loops affixed to free ends of the strap-like tensioning member pair, and a releasable means for affixing the brace to an existing garment like firefighting equipment.

U.S. Pat. No. 6,766,532 discloses a back support belt brace system comprised of a back panel, two side panels, two side wings, and a belt. The side wings are attached anywhere along the back panel and side panels using a hook and loop fastener providing adjustability. The belt is connected to the back panel, side panels, and two side wings with a hook and loop fastener. The belt contains an end with a belt buckle and an end with a plurality of holes, which are interlocked to secure the brace. An adjustable suspension system is attached to the support brace using clips.

U.S. Pat. No. 6,962,572 is directed to a lumbar support brace which is designed to create a tightening effect to push the abdominal contents and abdomen toward the spinal column. In addition, a U-shaped member supports the spine on either side and is connected to a pelvic support member so that the abdomen, spine, and pelvis are concurrently supported. The key feature of the present invention is that the support is a dynamic support which enables the wearer to engage in vigorously physical activity.

U.S. Pat. No. 7,134,969 discloses a device and method for encouraging or ensuring proper posture of a golfer during a golf swing. In certain embodiments, the device may be in the form of a brace comprising a strap that fits around the body to resist or prevent excessive bending of the spine, or "hunching over," during the golf swing. The brace may have a single, continuous strap that winds around the body, forming a crossing pattern across the spine and passing over both shoulders, with the ends of the strap meeting in the front of the body. The ends of the strap may be joined, for example by a buckle, to allow adjustment. The brace may be an integral part of a garment, which may have an outer shell and inner lining.

U.S. Pat. No. 8,708,834 is directed to a golf training harness. The harness comprises a body, two shoulder straps attached to the body, at least a waist strap either fixedly or removeably attached to the body, and a shaft; wherein the shaft is removeably inserted within a channel that extends the length of the body. When the user wears the harness, the shaft extends above and below the channel and the shaft contacts a back of the user's head, the user's scapular or upper back area, and the user's sacrum or lower back area, and these three points of contact of the shaft with the user's body enable the user to learn and achieve a proper golf posture and swing.

U.S. Pat. No. 7,651,163 is directed to lumbar support device comprising a rigid shell having a back portion between opposing sides, the sides extending forwardly of the back portion and defining a hollow, the rigid shell being formed from a rigid inelastic material; and an inelastic lumbar support surface for engaging a user's lumbar region having one end attached to one of the sides of the rigid shell and another end attached to the other side of the rigid shell such that the surface partially encloses the hollow, said surface having an adjustable surface contour configured to be adjusted to conform to a neutral postural position of a user's lumbar region.

U.S. Pat. No. 8,449,484 discloses a conformable brace used for supporting both the abdomen and lower back of a wearer in preventative and treatment applications. The brace includes an abdominal support panel substantially enclosed within a support envelope, a lumbar support panel having a dome-shaped protrusion that complements the lumbar contour of the user's back, and a belt that places the abdominal support panel and the lumbar support panel in opposed biasing arrangement against the torso of a user. The belt is associated with the support envelope and is also inserted though vertical slots in the lumbar support panel. The belt is used for selection of the biasing force needed by each user, the support envelope evenly distributes the tension provided by the belt across the abdominal support panel for enhanced user comfort, and a Y-shaped end tab comprising easily-releasable material helps the belt to remain secure during its use.

U.S. Pat. No. 8,226,587 discloses a spinal support, having a right arm having an abutment that is adapted to abut against an anterior portion of the right pelvic bone; and a left arm having an abutment that is adapted to abut against an anterior portion of the left pelvic bone; such that said abutment of said left arm is separated by a distance from said abutment of said right arm; wherein said right and left abutments are adapted to rest on said right and left anterior superior iliac spine, and a posterior spinal support adapted to abut against at least a portion of the spine, comprising a connector for connecting each of said left and right arms to said posterior spinal support; wherein said right and left abutments are essentially on a plane parallel to said posterior spinal support, therein generating and exerting a force in an a posterior to anterior direction between said right and left abutments and said posterior support; wherein said right and left arm are configured to minimize pressure on the lateral sides of the body; wherein at least one of said abutment of said one right arm or said abutment of said one left arm adjustably extends with respect to said one posterior spinal support; wherein at least one of said one right arm or said one left arm are adjustable to assume at least two angles with respect to the longitudinal axis of said one posterior spinal support.

While these above described devices may work for their intended purpose, there is a need for improved lumbar-pelvic-hip support devices which have the benefits of some known devices, yet none of the shortcomings. Unlike other knows devices, the instant invention is designed to support the pelvic region, the center of the kinetic chain that stabilizes our core and controls the body's balance in a novel manner.

Therefore, the present invention is directed towards improved lumbar-pelvic-hip support devices, in particular, devices useful for playing golf or other sports requiring flexibility and freedom of movement while maintaining the user's posture in an optimal position.

SUMMARY OF THE INVENTION

In one non-limiting embodiment, a lumbar-pelvic-hip support device comprises an elastic body. The body has an outer side, an inner side, a central region, and tapered ends. The tapered ends include hook and loop fasteners for fastening the body about a user's torso. A first X shaped member is connected centrally to the body and is configured to bisect the body. A longitudinal member is connected to the body and is configured to bisect the X shaped member. A pair of elastic straps is connected to the body. Each of straps includes an inner portion, an outer portion, and a terminal portion having fasteners. The inner portion is disposed substantially perpendicular to the Z axis of the body. The outer portion overlaps the inner portion and is disposed at an angle in the Z direction. The pair of straps can be fastened the outer side of the body using fasteners.

In one embodiment of this aspect, the device includes a second and a third X shaped member.

In some embodiments, the first X shaped member is disposed to bisect the body and the second and third X shaped members are disposed laterally on opposite sides of the first member.

In certain embodiments, the longitudinal member comprises a stiffener.

In some embodiments, the first X shaped member comprises a stiffener.

In other embodiments, the X members include a stiffener.

In yet other embodiments, the one or more X members and the longitudinal members include a stiffener.

In some embodiments, the stiffener can be a flexible material such as aluminum or a polymer. The stiffener can be internal or external to the body or integral with the body.

In some embodiments the X member or members can be anterior or posterior to the longitudinal I member.

In another aspect of the present invention, a lumbar-pelvic-hip support device includes a body. The body has an outer side, an inner side, a central region, and tapered end regions. The tapered end regions include hook and loop fasteners for fastening the body about a user's torso. An X shaped member is connected to the central region of said body and is configured to provide torsional support to said user's torso. An I shaped longitudinal member is disposed centrally on the body and bisects the X shaped member. A first and a second elastic strap are connected to the longitudinal member and the body. The first and second straps each include a terminal end having fasteners. The straps can be fastened to the outer side of said body to provide support to the user's torso.

In certain embodiments, the body comprises an elastic material.

In some embodiments, the X shaped member comprises an elastic material.

In some embodiments, the X shaped reinforcement member comprises an internal stiffener.

In other embodiments the I shaped member comprises an internal stiffener.

In several embodiments, the device includes a second and a third X shaped reinforcement members disposed symmetrically on opposite sides of the X shaped reinforcement member. The device can include a plurality of X members or I members.

In another aspect of the invention, a method of providing lumbar-pelvic-hip support comprises the steps of:

a) fastening an elastic body about a user's torso. The body has an outer side, an inner side, a central region, and tapered end regions. The tapered end regions includes hook and loop fasteners for fastening the body about a user's torso. The body includes an X shaped member having an internal stiffener. The X shaped member is connected to the central region of the body and is configured to bisect the body. The body includes an I shaped longitudinal member. The I shaped member is disposed centrally on the body and configured to bisect the X shaped member. The I shaped member includes an internal stiffener.

b) fastening a first end of a first elastic strap to the body. The first strap having a second end connected to the body. The first strap includes an inner portion, an outer portion, and a terminal portion having fasteners. The inner portion is disposed substantially perpendicular to the Z axis of the body. The outer portion overlaps the inner portion and is disposed at an angle in the (plus) Z direction.

c) fastening a first end of a second elastic strap to the body. The second strap having a second end connected to the body. The second strap includes an inner portion, an outer portion, and a terminal portion having fasteners. The inner portion is disposed substantially perpendicular to the Z axis of the body. The outer portion overlaps the inner portion and is disposed at an angle in the (plus) Z direction.

The invention is directed to an adjustable lumbar-pelvic-hip support garment for golfers, in particular, a device used to simultaneously support both the lumbar spine and pelvis with specific reinforcements.

In some embodiments, the device is designed to enhance a golfer's swing ability for those who may have, for example, a lower back or hip condition. A proper golf swing requires rotation and extension of the lumbar spine coupled with pelvic rotation. These motions can create or exacerbate spine or hip conditions.

Thus, the invention as described herein provides improved core and trunk alignment (i.e. spine and pelvis), which can assist a golfer in executing a proper golf swing while reducing the probability of injury.

Strategically placed supports can protect against excessive spinal twisting, tilting, over extension, or pelvic torque associated with the follow-through after striking the ball. Some control features as described below will also help reduce the strain placed on the lower back area thus preventing future injuries commonly associated with golf.

DETAILED DESCRIPTION

As used herein, the term "back support", refers to lumbar-pelvic-hip support. The center of activity in the human body for static weight bearing, normal biomechanics, and posture is the lumbar-pelvic-hip region. The sacrum is the seat of the transverse center of gravity, the keystone of the pelvis and the foundation for the spine.

In one non-limiting embodiment of the instant invention as depicted in FIGS. 1-7, a lumbar-pelvic-hip support device 100 comprises a symmetric elastic body 2 having a wider central control region 6 and tapered ends 10 for securing the device around a user's waist. The width of the central region is designed to extend from a superior area to an inferior area in order to provide synchronized, concurrent lumbar and pelvic support. As discussed below, the tapered ends can be used to secure the device about a user's waist using hook 12 and loop 13 fastener systems, such as VELCRO®, or other known connection means. It will be appreciated that the hook and loop portions of the fastening system can be interchanged to form a removable connection.

The body 2 includes outer portion 14 and inner portion 18. In this embodiment, the device includes three X shaped support members 22 and one I shaped vertical support member 26 that bisects the central X shaped member. Other arrangements of X supports and I supports are contemplated.

As depicted in FIGS. 1-4, the first and a third X members are disposed laterally and the second X member is disposed centrally bisecting the midline of body 2 between the first and third X members. The X members can be constructed of an elastic material to facilitate flexibility. In this embodiment, the central or second X member includes a flexible stiffening member 30 and can include a central pocket for retaining the stiffener. Stiffeners can be metallic or polymeric material design for providing additional longitudinal or torsional support. The lateral X members aid in absorbing the forces and minimizing the adverse effects of muscle recoil.

The vertical I shaped support member 26 is disposed centrally and posterior to bisect the central X. In this embodiment, the vertical I includes a longitudinal rectangular internal stiffener 30. This arrangement provides optimum longitudinal and torsional support for the lower back and pelvis.

Referring again to FIG. 1, the outside 14 of the device includes two elastic straps 34. The straps are anchored to the body near the midline proximate to the I support member. The straps comprise an offset loop that terminates with a hook 40 region that can be fastened to loop areas 13. In this way, the straps can be stretched and fastened to the loops on the body thereby creating secondary tension and support to the user. The body of the device is fastened about the user to create primary tension as discussed below.

Figure 2:
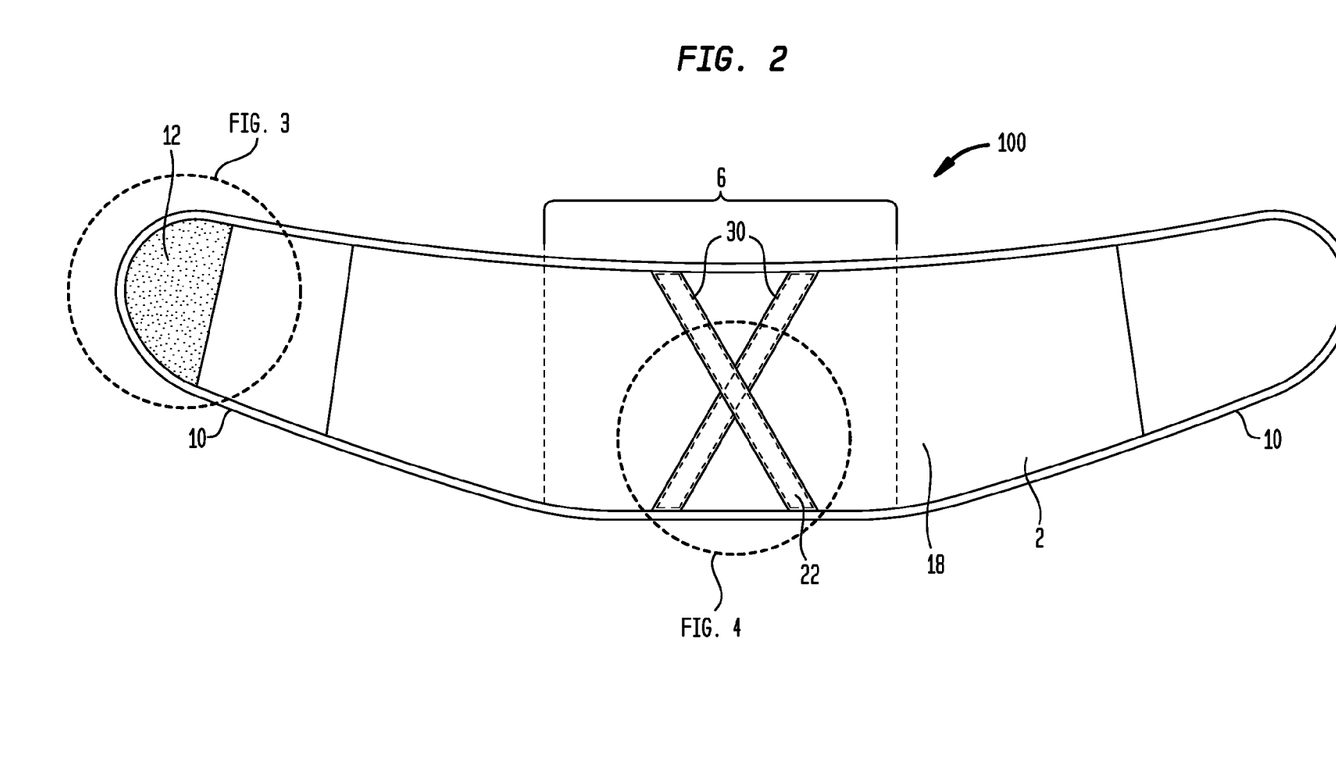
FIG. 2 depicts an inner side plan view of the embodiment shown in FIG. 1.
Figure 3:
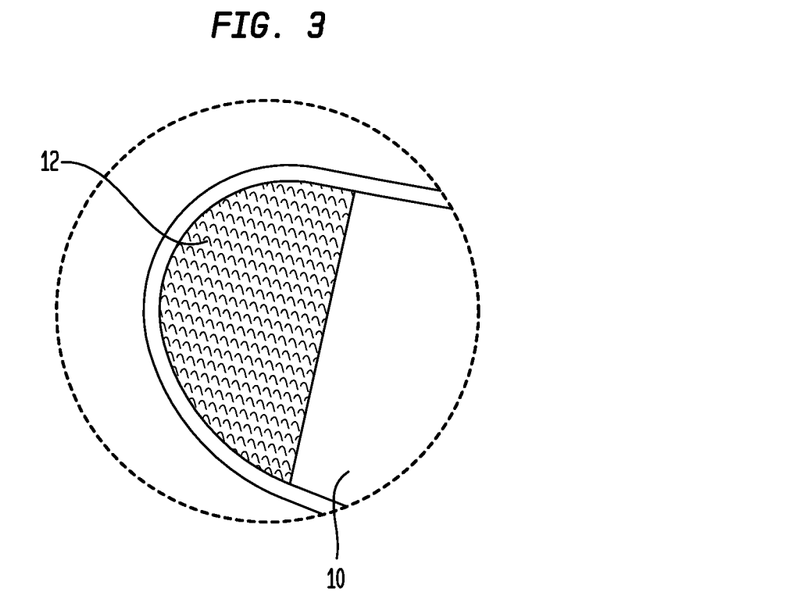
FIG. 3 depicts a detail view of some of the elements of the embodiment shown in FIG. 2.
Figure 4:
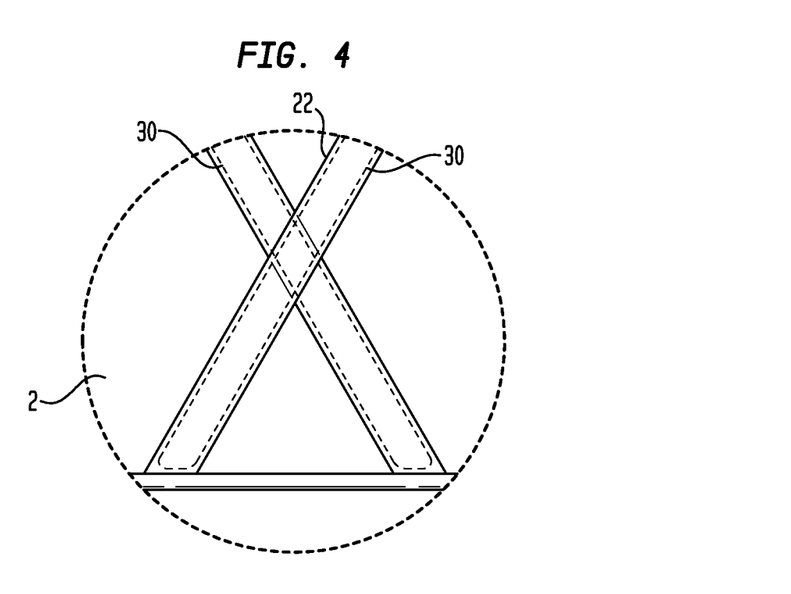
FIG. 4 depicts a detail view of some of the elements of the embodiment shown in FIG. 2.

Referring to FIGS. 2-4, the inside 18 of the device includes a hook type fastener portion 12 which can connect to the corresponding loop portion 13 on the outside 14 when the device is fastened about a user's 50 torso.

The arrangement of I shaped support members and X shaped support members will depend on the required amount of vertical and torsional support. The support can be adjusted by the use of different shapes or materials or stiffeners.

Of course, other embodiments having alternate configurations are contemplated to be within the scope of the instant invention. For example, the support members can be arranged XIX, IXIX, IXIXI, XIXIX, IIXIXII, or XXIIXXIIXX, and the like.

Figure 5:
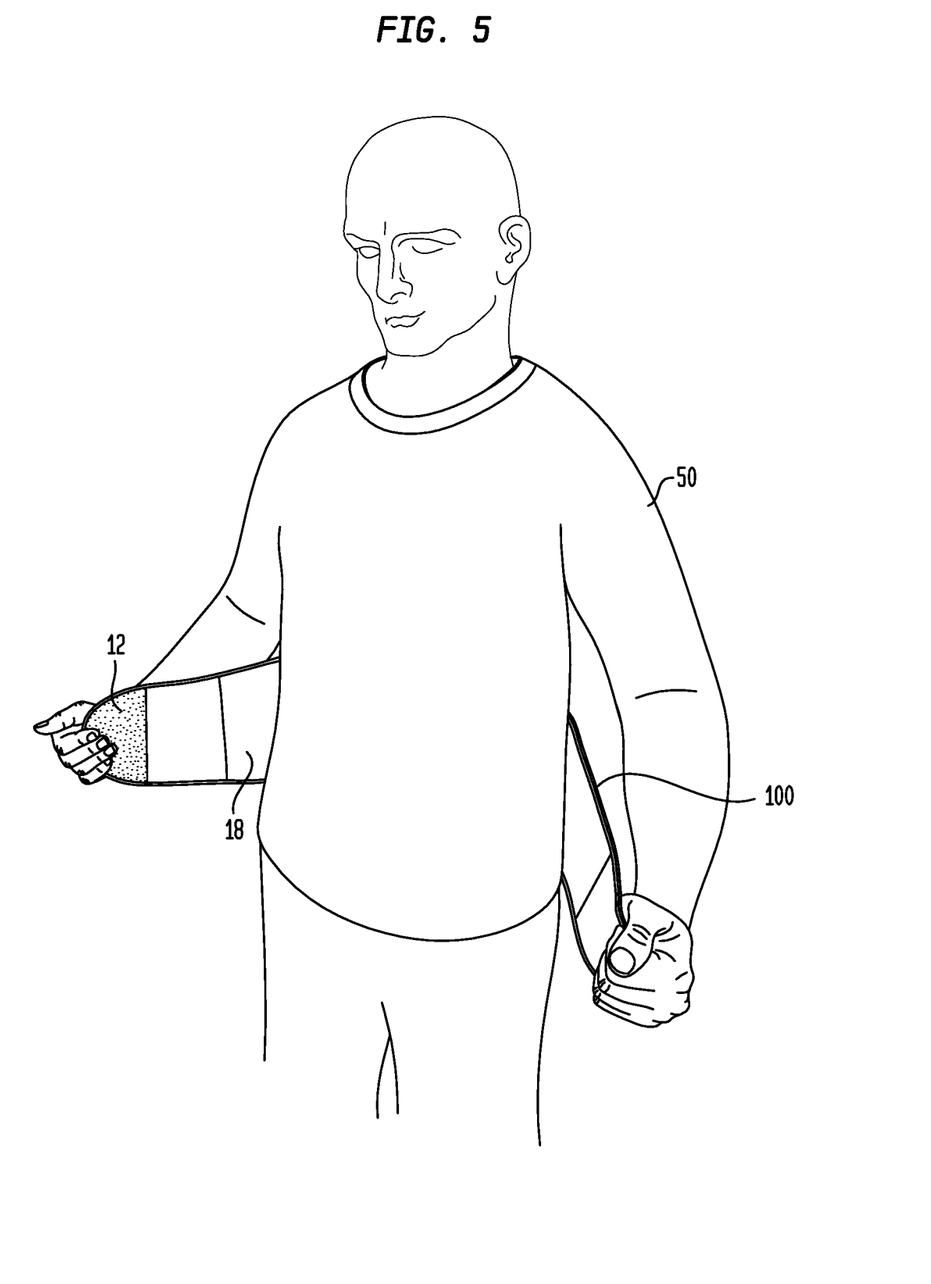
FIG. 5 depicts an isometric view of a user installing an embodiment of the invention.
Figure 6:
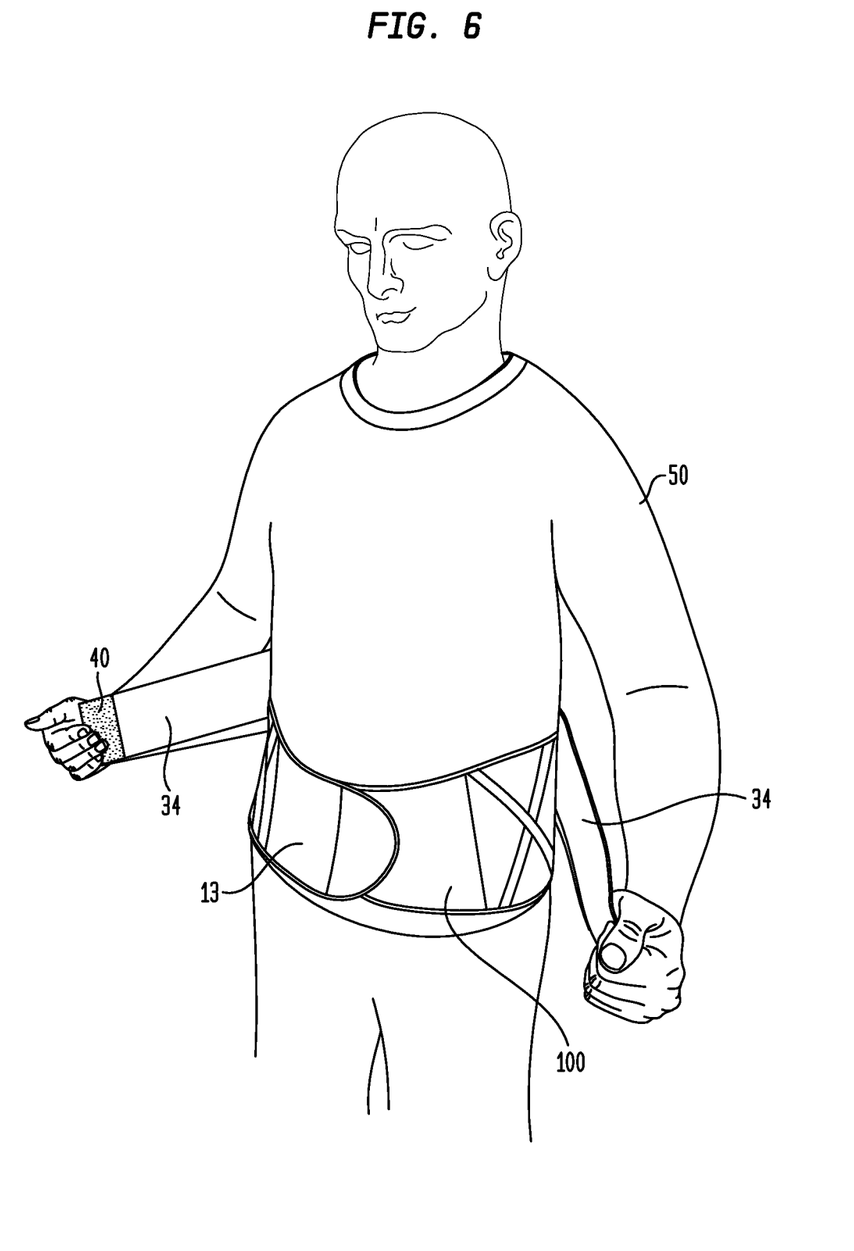
FIG. 6 depicts another isometric view of a user installing an embodiment of the invention.
Figure 7:
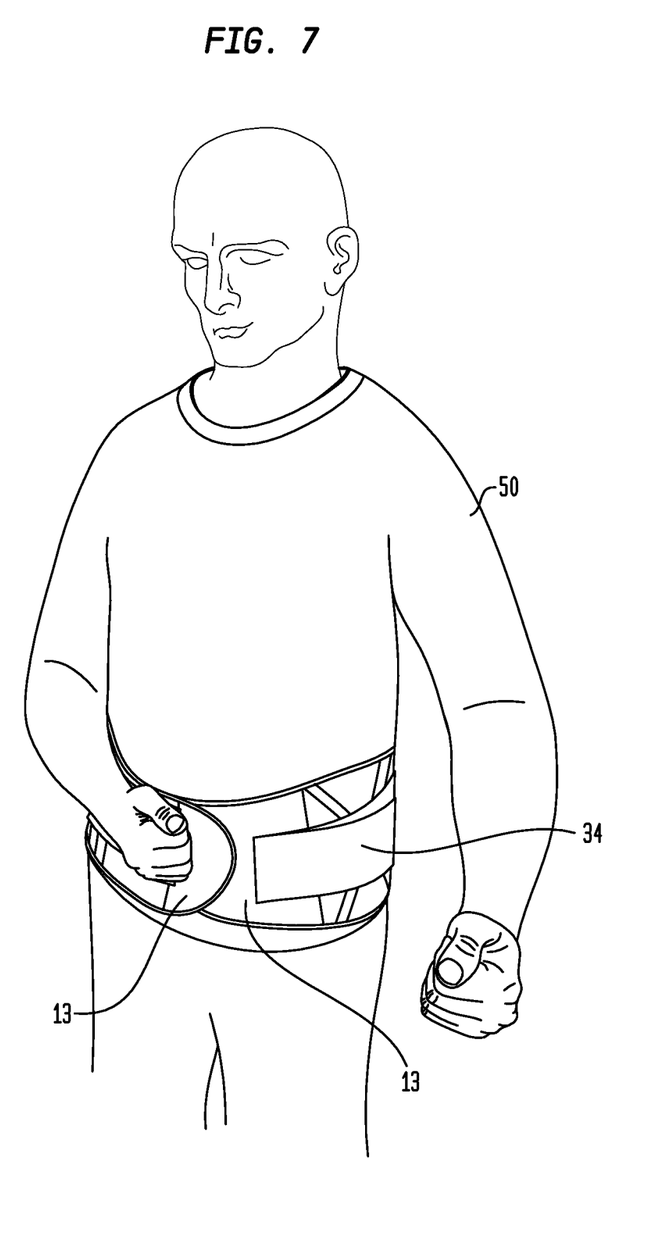
FIG. 7 depicts an isometric view of an embodiment of the invention installed about a user's waist area.

As shown in FIGS. 5-7, in operation, a user 50 positions the device 100 with the inner side 18 facing the user's torso. Next, the elastic body 2 of the device 100 is stretched and cinched or fastened around the mid-section (including the lumbar-sacral area) of the user, via the hook 12 and loop 13 fastening system. Of course, it will be known to a person of ordinary skill in the art that the hooks side and loop side of any hook and loop fastener system can be interchangeable.

Next, as shown in FIGS. 6 and 7, the user 50 can stretch the straps 34 to a comfortable and supported position and secure the straps to the outside of the body 18 via the corresponding hook and loop fasteners.

Figure 1:
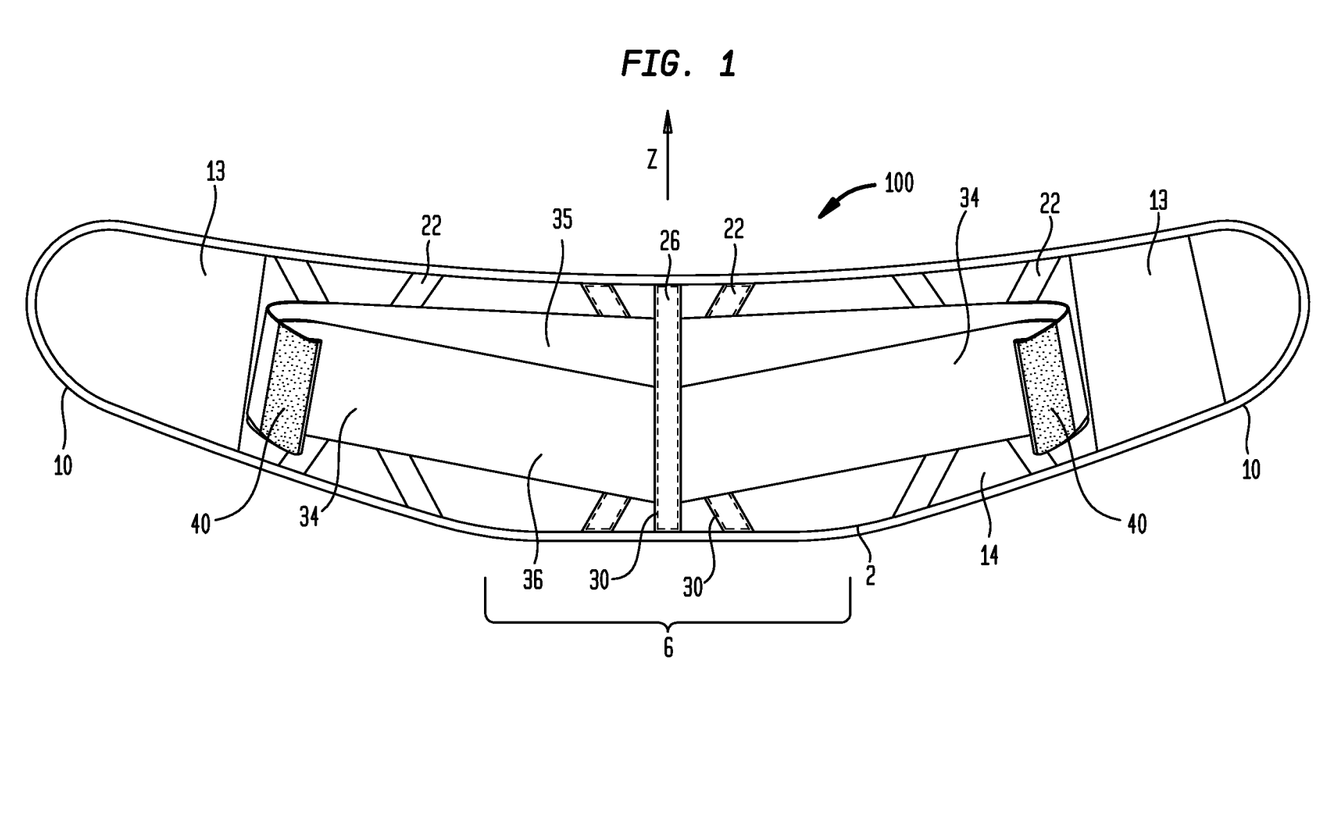
FIG. 1 depicts an outer side plan view of one embodiment of the present invention.

In this way, the device is secured about the user's body for primary support after which the straps are secured to the outside of the device for secondary support. The straps 34 each include a first portion 35 which is attached to the midline of the body and extends substantially perpendicular with the Z axis, as shown in FIG. 1 (and parallel with the long axis of the body 2). The first portion 35 can be positioned internally to the second portion 36.

The second portion 36 is attached to the midline of the body 2 at a position below (in the −Z direction) the first portion and overlaps the first portion (See FIG. 1). The second portion 36 of strap 34 is disposed in an angular relationship to the first portion 35 of strap 34 such that the first portion and the second portion overlap, the second portion being disposed at an angle disposed in a +Z direction (i.e. the direction towards a user's upper body). The first and second portions are joined together creating an end having hooks 40 for attachment of the straps to the loops 13 on the exterior of the body.

The position of first portion 35 and second portion 36 is critical to providing simultaneous circumferential support and torsional support to the user's core.

Removal of the device is easily accomplished by disconnecting the fasteners holding the body 2 about the user. Any of the primary fasteners (i.e. body fasteners, and two strap fastener) can be disconnected and reconnected to make adjustments at any time.

In this embodiment, the first and third X members are disposed on opposite sides or laterally on the user's body while the second member is disposed centrally and bisected by the I shaped support member, and posterior on the user's mid back.

In this way, the user is provided with longitudinal support, torsional support and circumferential support, of both the lumbar spine and pelvis while remaining flexible for a proper golf swing or any other contemplated activity. This arrangement allows the user to perform without feeling constrained, while training the user's body to attain a proper posture, thus creating an awareness of proper posture and minimizing risk of injury.

Optionally, the device can include a breathable hypoallergenic elastic fabric comprising the central region. A hypoallergenic moisture absorbing fabric can comprise the distal regions proximate to the fastening means.

The X or I support members can include any flexible material that can provide the required level of support, such as a metallic or polymeric material, and may be covered with fabric or encapsulated within the elastic fabric body support. The vertical supports can also be made using any suitable materials such as metallic (e.g. aluminum) or polymeric materials and can be covered with a rubberized fabric. The support members can be integral with the device body structure or mounted to, or encapsulated within the structure as depicted in this embodiment.

It is contemplated that the torsional and longitudinal elements can take the form of other shapes, such as, for example a Y shape or and S shape for the torsional element and an L or upside down L shape for the longitudinal support. Alternate arrangements of elements, for example can be YLLYLLY or SIISIIS and the like.

The strategically placed longitudinal and torsional support elements will protect against excessive spinal twisting, tilting, over extension, and pelvic torque associated with the follow through after hitting a golf ball. With improved the control, the overall golf swing will be enhanced. The control features can also help reduce the strain placed on existing low back area orthopedic issues and aid in the prevention of future conditions commonly associated with golf or other sports.

The device may be manufactured by known manufacturing methods using materials including, for example, polymeric materials such as polyesters, elastodienes, and nylons. In one embodiment, the device comprises about 75% polyester, about 20% elastodiene, and about 5% nylon. In some embodiments, the elastic fabric portions of the device can be about 79% polyester and about 21% elastodiene. Elastodiene is an elastofibre composed of natural or synthetic polyisoprene, or composed of one or more dienes polymerized with or without one or more vinyl monomers, and which, when stretched to three times its original length and released, recovers rapidly and substantially to its initial length.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. A lumbar-pelvic-hip support device comprising:
   (a) a body, said body having an outer side, an inner side, a central region, a Z axis and tapered end regions, said tapered end regions including hook and loop fasteners configured for fastening said body about a user's torso;
   (b) an X shaped member, said X shaped member including a central pocket, said X shaped member including an X shaped flexible internal stiffener retained within said central pocket, said X shaped member being connected to said central region of said body between said outer side and said inner side and extending across the body in the Z axis direction, and being configured to provide torsional support to said user's torso;
   (c) an I shaped longitudinal member, said I shaped member including a central pocket and a flexible internal stiffener retained therein, said I shaped member being disposed centrally on said outer side of said body and bisecting said X shaped member; and
   (d) a first and a second elastic strap being connected to said longitudinal member and said body, said first and second straps each include a terminal end having fasteners, wherein said straps can be fastened to said outer side of said body to provide support to said user's torso.

2. The device of claim 1, wherein said body comprises an elastic material.

3. The device of claim 1, wherein said X shaped member comprises an elastic material.

4. The device of claim 1, further including a second and a third X shaped member disposed symmetrically on opposite sides of said X shaped member.

5. A lumbar-pelvic-hip support device comprising:
   (a) an elastic body, said body having an outer side, an inner side, a central region, a Z axis, and tapered ends, said tapered ends including hook and loop fasteners configured for fastening said body about a user's torso;
   (b) a first X shaped member, said X shaped member including a central pocket, said X shaped member including an X shaped flexible internal stiffener retained in said central pocket, said X shaped member being connected centrally to said body between said outer side and said inner side and being configured to bisect said body;
   (c) a longitudinal member, said longitudinal member including a central pocket and a flexible internal stiffener retained therein, said longitudinal member being connected to said outer side of said body and being configured to bisect said X shaped member; and
   (d) a pair of elastic straps being connected to said body, each of said straps including an inner portion, an outer portion, and a terminal portion having fasteners, said inner portion being disposed substantially perpendicular to the Z axis of said body, said outer portion overlapping said inner portion and being disposed at an angle in the Z axis direction, wherein said pair of straps can be fastened to said outer side of said body using said fasteners.

6. The device of claim 5, further including a second and a third X shaped member.

7. The device of claim 6, wherein said first X shaped member is disposed to bisect said body and said second and third X shaped members are disposed laterally on opposite sides of said first member.

8. A method for using a lumbar-pelvic-hip support comprising:
   (a) fastening an elastic body about a user's torso, said body having an outer side, an inner side, a central region, a Z axis, and tapered end regions, said tapered end regions including hook and loop fasteners for fastening said body about a user's torso; said body including an X shaped member having an internal stiffener, said X shaped member being connected to said central region of said body between said outer side and said inner side and being configured to bisect said body, said body including an I shaped longitudinal member, said I shaped member being disposed centrally on said body and configured to bisect said X shaped member, said I shaped member including an internal stiffener;
   (b) fastening a first end of a first elastic strap to said body, said first strap having a second end being connected to said body, said first strap including an inner portion, an outer portion, and a terminal portion having fasteners, said inner portion being disposed substantially perpendicular to the Z axis of said body, said outer portion overlapping said inner portion and being disposed at an angle in the Z direction; and
   (c) fastening a first end of a second elastic strap to said body, said second strap having a second end being connected to said body, said second strap including an inner portion, an outer portion, and a terminal portion having fasteners, said inner portion being disposed substantially perpendicular to the Z axis of said body, said outer portion overlapping said inner portion and being disposed at an angle in the Z direction.

* * * * *